(12) United States Patent
Freudenthal

(10) Patent No.: US 11,938,300 B2
(45) Date of Patent: Mar. 26, 2024

(54) DEVICE FOR THE DOSED DISPENSING OF AN INFUSION FLUID

(71) Applicant: PFM MEDICAL AG, Cologne (DE)

(72) Inventor: Franz Freudenthal, La Paz (BO)

(73) Assignee: PFM MEDICAL AG, Cologne (DE)

( * ) Notice: Subject to any disclaimer, the term of this patent is extended or adjusted under 35 U.S.C. 154(b) by 0 days.

(21) Appl. No.: 15/326,321

(22) PCT Filed: May 15, 2015

(86) PCT No.: PCT/EP2015/060751
§ 371 (c)(1),
(2) Date: Jan. 13, 2017

(87) PCT Pub. No.: WO2016/008614
PCT Pub. Date: Jan. 21, 2016

(65) Prior Publication Data
US 2017/0203035 A1    Jul. 20, 2017

(30) Foreign Application Priority Data

Jul. 16, 2014 (DE) ..................... 20 2014 103 278.9

(51) Int. Cl.
*A61M 5/168* (2006.01)
*A61M 5/14* (2006.01)
(Continued)

(52) U.S. Cl.
CPC ...... *A61M 5/16818* (2013.01); *A61M 5/1415* (2013.01); *A61M 5/16845* (2013.01);
(Continued)

(58) Field of Classification Search
CPC ........ A61M 5/16818; A61M 2039/229; A61M 2205/3393; A61M 2209/08; A61M 5/36
See application file for complete search history.

(56) References Cited

U.S. PATENT DOCUMENTS

| | | | |
|---|---|---|---|
| 2,771,878 A | | 11/1956 | Folland et al. |
| 3,074,451 A | * | 1/1963 | Whitney .................. A61J 1/10 73/426 |

(Continued)

FOREIGN PATENT DOCUMENTS

| | | |
|---|---|---|
| CN | 100462110 | 2/2009 |
| DE | 7610866 | 12/1976 |

(Continued)

OTHER PUBLICATIONS

Nave, R., Poiseuille's Law, Accessed Apr. 11, 2019, http://hyperphysics.phy-astr.gsu.edu/hbase/ppois.html (Year: 2000).*

(Continued)

*Primary Examiner* — Lauren P Farrar
(74) *Attorney, Agent, or Firm* — Grossman, Tucker, Perreault & Pfleger, PLLC

(57) ABSTRACT

The invention relates to a device for the dosed dispensing of an infusion fluid, in particular for administering an infusion for a patient, comprising a fluid vessel for accommodating the infusion fluid, and comprising an infusion line which is arranged between the fluid vessel and a patient access during the use of the device, wherein the fluid vessel and the infusion line are connected to one another, and the infusion line is designed such that at least a sub-section of the infusion line has a predefined inner diameter and a predefined length, such that the amount of infusion fluid accommodated in the fluid vessel is dispensed to the patient access over a predetermined time period in a manner dependent on a predefined height at which the fluid vessel is arranged above the patient access.

26 Claims, 5 Drawing Sheets

(51) Int. Cl.
*A61M 5/36* (2006.01)
*A61M 25/00* (2006.01)
*A61M 39/22* (2006.01)

(52) U.S. Cl.
CPC .......... *A61M 5/36* (2013.01); *A61M 25/0045* (2013.01); *A61M 2039/229* (2013.01); *A61M 2205/3393* (2013.01); *A61M 2209/08* (2013.01)

(56) References Cited

U.S. PATENT DOCUMENTS

| | | | | |
|---|---|---|---|---|
| 3,425,415 | A * | 2/1969 | Gordon | A61M 5/142 |
| | | | | 604/153 |
| 3,690,318 | A | 9/1972 | Gorsuch | |
| 4,034,754 | A | 7/1977 | Virag | |
| 4,116,646 | A | 9/1978 | Edwards | |
| 4,306,976 | A * | 12/1981 | Bazzato | A61M 1/285 |
| | | | | 210/646 |
| 4,650,452 | A | 3/1987 | Jensen | |
| 4,863,437 | A | 9/1989 | Clarke | |
| 4,979,644 | A * | 12/1990 | Meyer | A61M 5/16818 |
| | | | | 222/129 |
| 5,496,283 | A * | 3/1996 | Alexander | A61M 25/02 |
| | | | | 604/180 |
| 5,910,135 | A | 6/1999 | Hadzic et al. | |
| 6,013,061 | A | 1/2000 | Kelley | |
| 6,371,937 | B1 * | 4/2002 | McPhee | A61M 5/16854 |
| | | | | 604/118 |
| 6,422,529 | B1 | 7/2002 | Adelberg | |
| 6,569,128 | B1 * | 5/2003 | Christensen | A61M 5/16804 |
| | | | | 604/246 |
| 7,753,884 | B2 | 7/2010 | Gallnboeck | |
| 2002/0038392 | A1 * | 3/2002 | De La Huerga | G16H 20/17 |
| | | | | 710/8 |
| 2004/0116846 | A1 | 6/2004 | Olivera et al. | |
| 2006/0155249 | A1 | 7/2006 | Hishikawa et al. | |
| 2007/0235623 | A1 * | 10/2007 | Amisar | A61J 1/1462 |
| | | | | 248/560 |
| 2012/0245563 | A1 * | 9/2012 | Lareau | A61M 25/0026 |
| | | | | 604/533 |
| 2014/0231301 | A1 * | 8/2014 | Herbert | A61J 1/03 |
| | | | | 156/60 |
| 2015/0257975 | A1 * | 9/2015 | Sung | A61J 1/16 |
| | | | | 220/500 |

FOREIGN PATENT DOCUMENTS

| | | |
|---|---|---|
| DE | 2621542 | 3/1977 |
| DE | 3035301 | 4/1981 |
| DE | 8608893 | 10/1986 |
| DE | 19955368 | 5/2001 |
| EP | 0042431 | 3/1985 |
| EP | 1428541 | 6/2004 |
| GB | 2059776 | 4/1981 |
| WO | 2005/011778 | 2/2005 |
| WO | 2009/131266 | 10/2009 |

OTHER PUBLICATIONS

International Search Report from corresponding PCT Appln. No. PCT/EP2015/060751, dated Aug. 4, 2015.
Notice of Allowance from related Canadian Appln. No. 2,985,389, dated Sep. 7, 2022.
Office Action from related EPO Appln. No. 15722224.1, dated Apr. 29, 2019. English translation attached.
Office Action from related EPO Appln. No. 15722224.1, dated May 20, 2022. English translation attached.

* cited by examiner

DEVICE FOR THE DOSED DISPENSING OF AN INFUSION FLUID

FIELD OF THE INVENTION

The invention relates to a device for the dosed dispensing of an infusion fluid, in particular for administering an infusion for a patient.

BACKGROUND

Devices for the dosed dispensing of infusion fluids are known from the prior art in different kinds. For example WO 2005/011778 A1 proposes a device, which consists of two parts connected to each other, from which one builds a pressure chamber and the other one is designed to receive replaceable infusion bags. The pressure chamber and the infusion bag received in the device are separated by a membrane. The device further has a gas pressure resource, which can exert a pressure to the infusion bag over the membrane, so that a dosed dispensing of the fluid contained in the infusion bag is achieved.

Further, device of the above mentioned kind are known, where the dispensing of the infusion fluid to a patient is regulated by a regulator device placed on the infusion line of the infusion bag. For this purpose the diameter of the infusion line is reduced or increased by a squeezing/clamping device at the infusion line.

Furthermore, infusion pumps are used for the dosed dispensing of infusion fluids, wherein the infusion fluid to be dispensed, which is for example contained in a syringe, is inserted into the device. The syringe can be actuated in a controlled manner by a sliding mechanism.

Disadvantages of the devices known from the prior art is that the dosing of the infusion fluid is poorly adjustable or if an better dosing is possible, like for example using the infusion pump, the device is very complex in design and use and due to the complexity expensive to manufacture.

Starting from this prior art it is an object of the present invention to provide a device for the dosed dispensing of an infusion fluid, which allows an accurate dosing of the infusion fluid to be dispensed and considering an easy and user friendly handling and an inexpensive manufacturing.

SUMMARY

The object is solved by a device as mentioned above in that the device comprises a fluid vessel for accommodating the infusion fluid, an infusion line, which is located between the fluid vessel and a patient access during use, wherein the fluid vessel and the infusion line are connected to each other, and the infusion line is designed such that at least a subsection of the infusion line has a predefined inner diameter and a predefined length, such that the amount of infusion fluid accommodated in the fluid vessel is dispensed to the patient access over a predetermined time period in a manner dependent on a predefined height at which the fluid vessel is arranged above the patient access.

The invention bases on the findings that a dosed dispensing of an infusion fluid particularly simplified if the dosing and thus the time period, in which the infusion fluid is dispensed, is predetermined. According to the invention therefore different parameters, which have an influence on the dosed dispensing of the infusion fluid, are already predetermined. An adaption of the dosing by a user is thus not provided. For use different embodiments of the device are provided for selection, which each allow dispensing of an infusion fluid over a predetermined but different time period. The user only has to choose the desired parameters, which are for example provided readable on the device, and which meets the requirements. Advantageously application errors during dosing can be avoided by the pre-configuration, since for example the difficult adjustment of complex devices known from the prior art can be omitted.

In an embodiment of the invention the device comprises a filter for the infusion fluid accommodated in the infusion vessel. Preferably the filter for the infusion fluid is located between the fluid vessel of the device and the infusion line connected to the fluid vessel.

In a further embodiment of the invention the fluid vessel and the infusion line are inextricably linked to each other.

Advantageously the predetermined time period, in which the infusion fluid is dispensed to the patient access, is determined by the inner diameter of the infusion line and/or the length of the infusion line. In practical tests in has been proven that particularly these two have a great influence on the amount of infusion fluid dispensed to the patient access. Further parameters in descending relevance regarding the influence to the dosed dispensing of the infusion fluid are the height difference between the patient access and the outlet opening of the fluid vessel, the ambient temperature, which affects the viscosity of the infusion fluid, as well as the content of the fluid vessel itself, hence which fluid or which kind of fluid contained in the infusion vessel. A further parameter which has an influence on the dosed dispensing of the infusion fluid is the actual pressure in the blood vessel, a vein or artery, of the patient. Accordingly a counter pressure can act in the form of a counter flow through the patient access onto the infusion fluid to be dispensed over the patient access, which can result in that the dispensing of the infusion fluid is slowed down.

A preferred embodiment of the invention is characterized in that the time period, in which the infusion fluid is dispensed to the patient access, is about 1 litre dispensed infusion fluid in 24 hours to about 1 litre in 6 hours, preferably about 1 litre in 8 hours, 12 hours, 18 hours, 15 hours or 3 hours. In this magnitude typical applications in the clinical day-to-day life are situated. Advantageously different inventive devices with different dosages and thus different dispensing time periods are stockpiled by the users, so that these can be easily selected by the users depending on the specific application. In a further embodiment the height (X) is about 60 cm to about 80 cm, preferably about 64 cm to 76 cm, particularly preferred 64 cm, 68 cm or 76 cm.

A preferred embodiment of the invention is characterized in that the infusion line has a stopcock, preferably in the area of the patient access.

A further embodiment of the invention provides that the fluid vessel is an infusion bag. Infusion bags can contain different infusion solutions for an infusion therapy. Next to an infusion therapy they can also contain infusion fluids for a parenteral nutrition. Further they can be carrier solutions, which can be mixed with an active substance, to achieve a particular administration of the active agent concentration over a predefined time period.

An advantageous embodiment of the invention provides that the fluid vessel and the fluid line are free of gases, in particular of air. Hereto a further embodiment of the invention can provide that the device has a venting, particularly a venting valve, which can free the device of gases in particular of air. Advantageously the venting is located at the upper end of the device, so that the venting of the device is simplified. Particularly it must be guaranteed that air is administered to the patient over the patient access. This can result in serious complications including the death of the patient. The manufacturing of infusion bags, which contain a vacuum and thus do not contain air, is known from the prior art. These are usually easy in manufacturing.

A further embodiment of the invention provides that the infusion line has a stopcock, preferably in the area of the patient access. Using such a stopcock the infusion line is sealable, so that the exiting of infusion fluid can be prevented. Particularly during the placing of the patient access, as well as the removal of the patient access, the usage of the device is much simplified if the stopcock prevents the exiting of infusion fluid.

A preferred embodiment of the invention provides that the device is a so-called single-use system designed for a one-time use. The inventive device thus has all components that are necessary for an infusion therapy. Presently this is a fluid vessel with an infusion fluid, an infusion line, by which the infusion fluid is removable from the infusion vessel, and a patient access, for example in the form of a peripheral venous catheter, by which the infusion fluid can be administered intravenously to the patient. Such single-use systems can be stockpiled and be used in case of need. Single-use systems are widespread in the daily clinical practice, due to the hygiene standards. Additionally such single-use systems are particularly cheap in manufacturing. Advantageously at least partly the components of the device designed as a single-use system are sterile.

According to the invention it can be provided that about 10% of the volume of infusion fluid that is planned to be administered to the patient remains in the infusion bag as a reserve. This can be used to have more time for the replacing of the inventive device, particularly to provide the nursing staff a time reserve for replacing, if it is envisaged to administer more infusion fluid than the amount of infusion fluid contained in the infusion bag. A further reason is that in case of an interruption of the flow or dispensing of the infusion fluid a coagulation of blood in the patient access can occur and thus block the access to the patient.

Further it can be provided that the patient access and thus the inventive device can be applied in different vessels of a patient, for example in a vein or an artery.

An advantage of the inventive device is that no contamination of the patient with germs, viruses or such the like is possible, since a manipulation of the inventive device is not possible due to the advantageous one-piece design.

The infusion bag of the inventive device can be very flexible; particularly it can consist of a soft plastic. Therefore no former usually used bottles with infusion fluid for dosed dispensing to a patient are necessary anymore. This has the particular advantage that a venting, which is necessary for bottles, is not necessary according to the invention.

A further embodiment of the invention provides that multiple infusion bags are connectable to an infusion line, for example using a so-called three-way-tap at a patient access, wherein preferably the different infusion bags have different predetermined time periods for the infusion fluids in the infusion bags.

Further, it can be provided that the inner surface of the infusion line is neutral, hydrophilic or hydrophobic.

In an advantageous embodiment of the invention the fluid vessel is arranged at a scale, which can determine the weight of the fluid vessel arranged at the scale.

Furthermore, the scale can comprise a display device, which is preferably designed for displaying the weight of the fluid vessel arranged at the scale and/or for displaying the fluid amount of the fluid vessel arranged at the scale.

A further embodiment of the invention provides that the device comprises a height adjustment, which can adjust the height of the fluid vessel above the patient access as a function of the weight of the fluid vessel, so that the time period in which the infusion fluid is administered to the patient access is adjustable. For the height adjustment of the inventive device the holder, which is used to mount the infusion vessel to the scale, can be rotated, pivoted or moved essentially in a vertical direction, so that a change of the height of the inventive device is performed. Further, the height adjustment can be located outside the scale, for example by providing a mechanism which can for example adjust the height of a stand on which the inventive device is locatable.

A further embodiment of the invention provides that the weight of the fluid vessel located at the scale is measured in predefined intervals, preferably in regular intervals, and particularly preferred constantly, so that according to the weight change the height can be adjusted.

In a further embodiment of the invention the device comprises a stopwatch, which can measure for example a single or complete time period for a partial or complete emptying of the fluid vessel.

An embodiment of the invention is characterized in that a control lamp or multiple control lamps are provided. For example in form of a traffic light with the colours red, yellow and green, which can indicate whether the dosing of the infusion fluid in the fluid vessel complies with the predetermined time. The control lamp or control lamps can thus fulfil warning functions, so that an error, for example a malfunction, is identified. Preferably in addition an optical and/or acoustic alarm can be provided, so that an optical and/or acoustic display device can indicate signals representing the alarm.

A further embodiment of the invention provides a control unit. This is for example programmable according to the specifications of the user of the inventive device. Advantageously the programmable specifications correspond to the parameter, which have according to the invention an influence on the dispensing of the infusion fluid in the infusion vessel. Thus, the measuring of the weight of the infusion vessel located at the scale can be controlled or regulated. Further, as a result the height adjustment of the inventive device can take place.

An embodiment of the invention comprises a start-/stop-button or an on-/off-switch, which can activate or deactivate the control unit and/or the scale and/or the height adjustment, preferably additionally the height adjustment and/or the weight measuring of the infusion vessel at the scale is adjustable.

Further details, features and advantages of the invention will be explained in the following with respect to the embodiments shown in the figures.

Figure 4B:
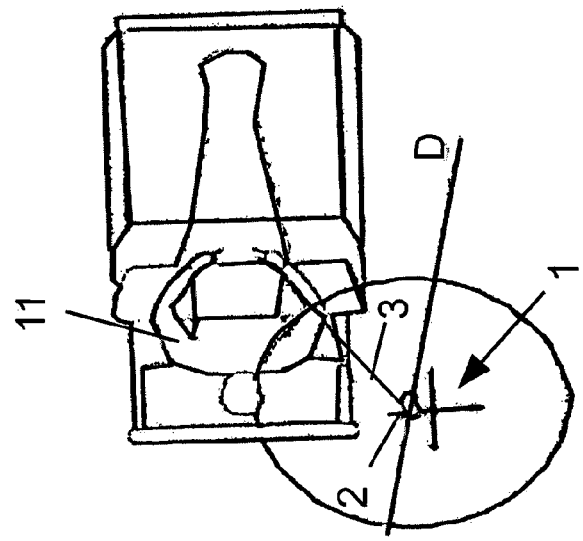
Figure 4A:
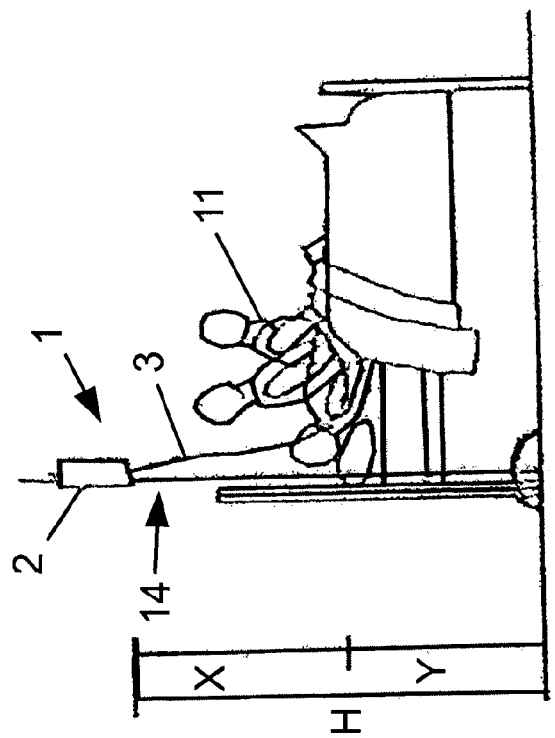
Figure 5:
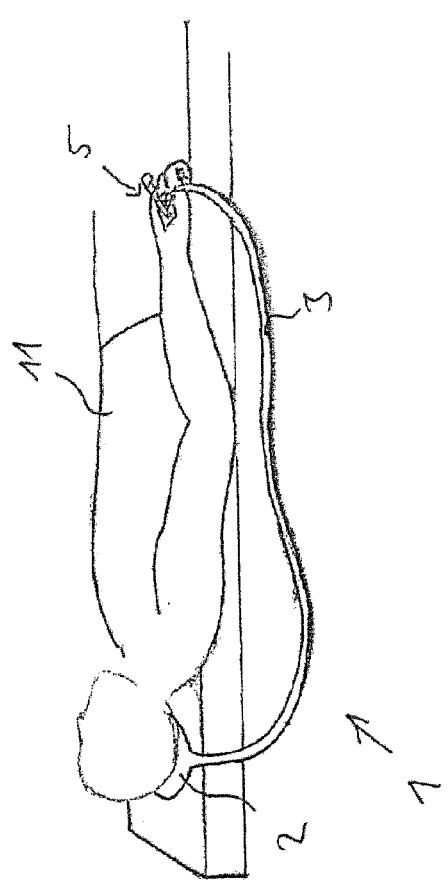

FIGS. 4a,b are views for illustrating the parameter influencing the dispensing time period; and FIG. 5 is a use of an embodiment of a device according to the invention with a patient.

DETAILED DESCRIPTION

Figure 1:
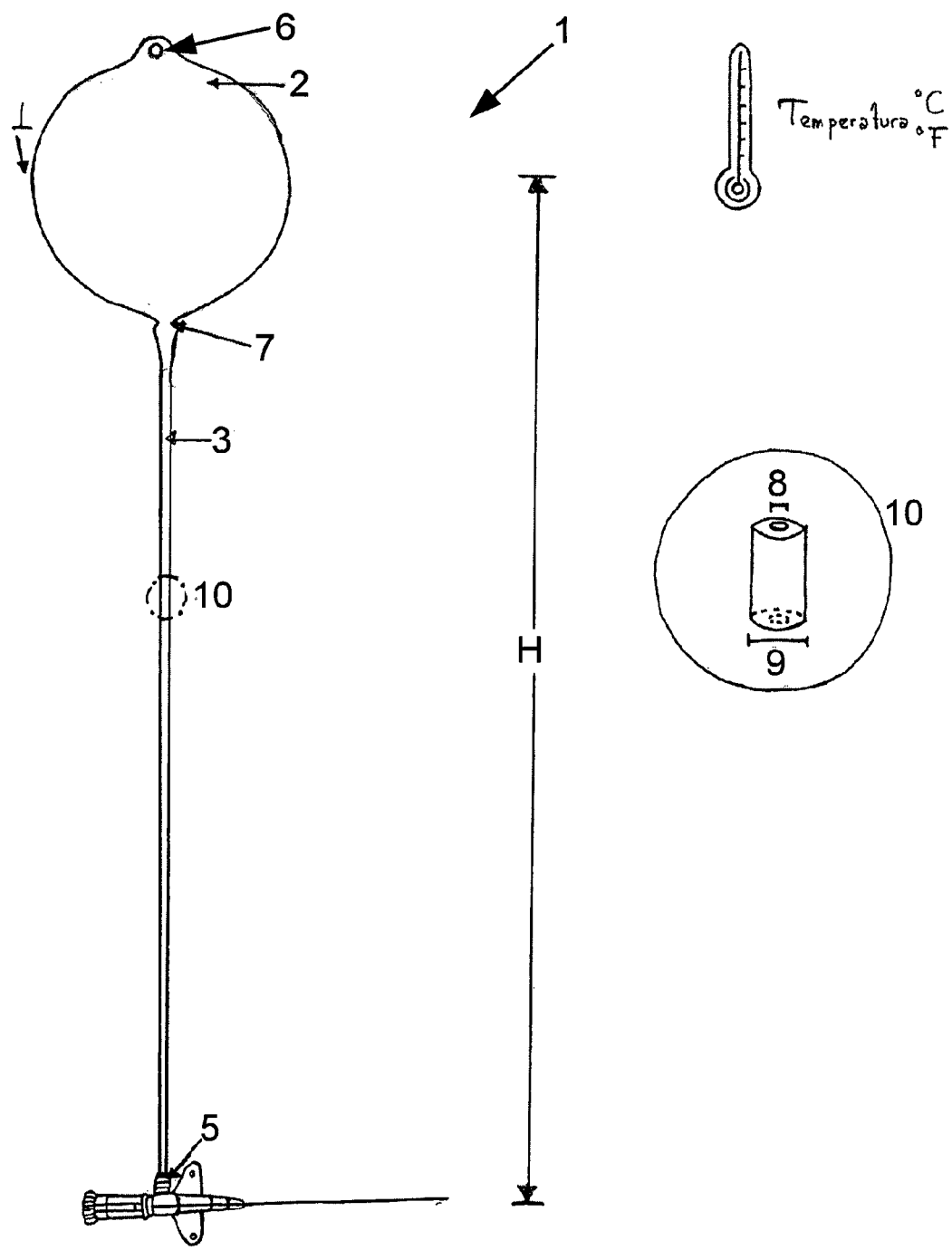
FIG. 1 is a schematic view of a device according to the invention.
Figure 2:
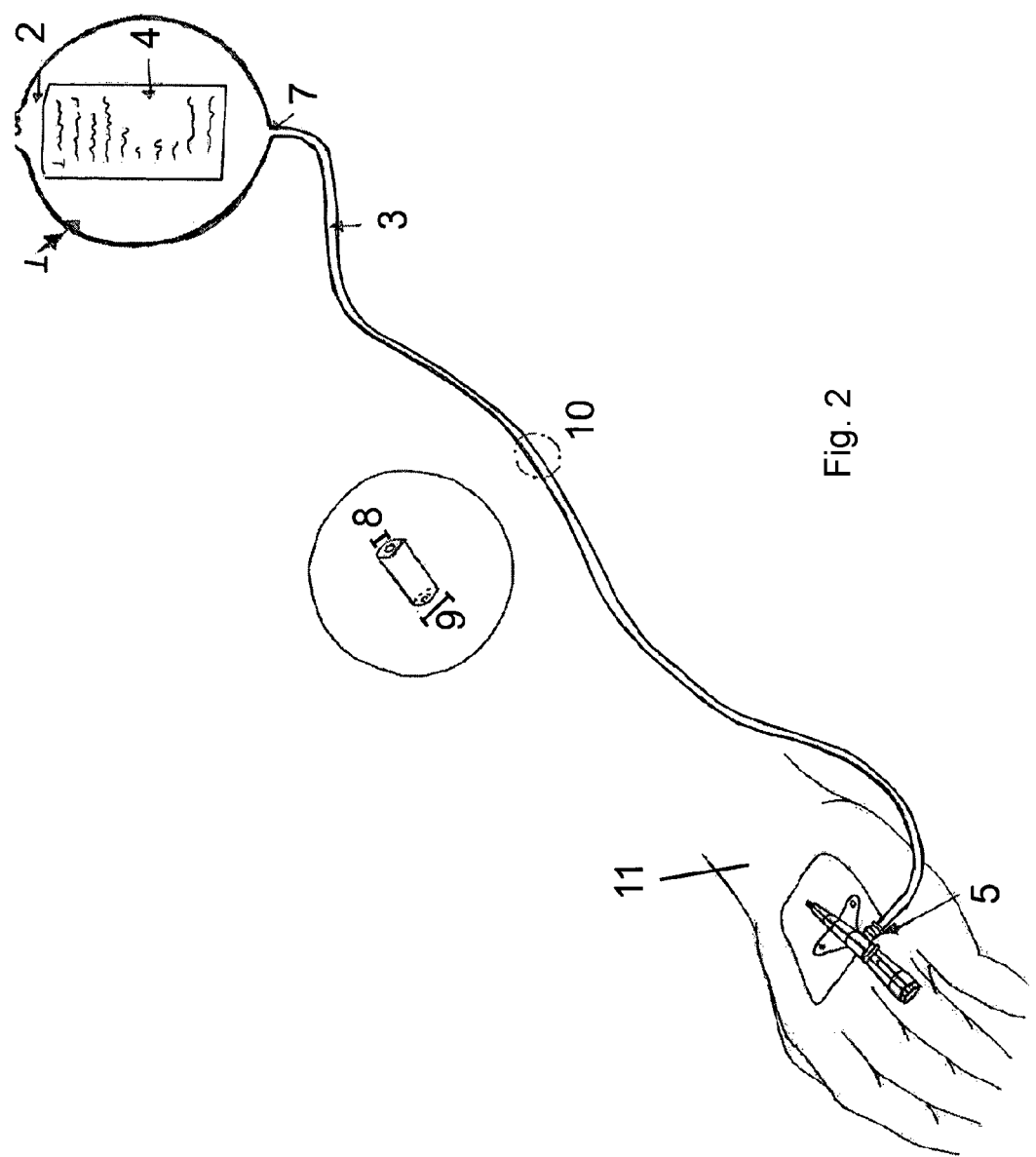
FIG. 2 is a further schematic view of a device according to the invention.

FIG. 1 and FIG. 2 show a device 1 according to the invention with an infusion bag 2, an infusion line 3 and a peripheral venous catheter 5. The infusion bag 2 has an infusion fluid. The infusion line 3 is located between peripheral venous catheter 5 and the infusion bag 2 and inextricably linked with the peripheral venous catheter 5 as well as with the infusion bag 2.

The inventive device 1 is designed such that the infusion fluid accommodated in the infusion bag 2 is dispensed to the peripheral venous catheter 5 and over this to a patient 11 in a predetermined time period.

The infusion line 3 has therefore a predefined inner diameter 8. This can be seen from the exemplary enlargement or detail view of the infusion line 3, wherein from this further the thickness of the infusion line, also referred to as diameter of the infusion line 9, can be identified. Furthermore, the dosed dispensing of the infusion fluid is defined by the length L of the infusion line 3, which is presently defined by the height H.

Further, the dosed dispensing of the infusion fluid is defined by the height X between the peripheral venous catheter 5 and the outlet opening or connection point 7 between the infusion line 3 and the infusion bag 2.

The infusion bag further has at its upper end a holder 15, which can be used to mount the infusion bag 2 to a s-called IV-stand.

On the infusion bag 2 a dosage instruction 4 is provided, which identifies the time period over which the infusion fluid of the infusion bag 2 is dispensed, thus it represents an instruction regarding the dosed dispensing of the infusion fluid. Preferably the dosage instruction 4 indicates information about the amount of infusion fluid in the fluid bag, like for example 1 litre and the predetermined time period over which the infusion fluid is dispensed over the peripheral venous catheter 5 to a patient 11. This can contain for example information like 'in 24 hours' or 'in 8 hours'.

Figure 3:
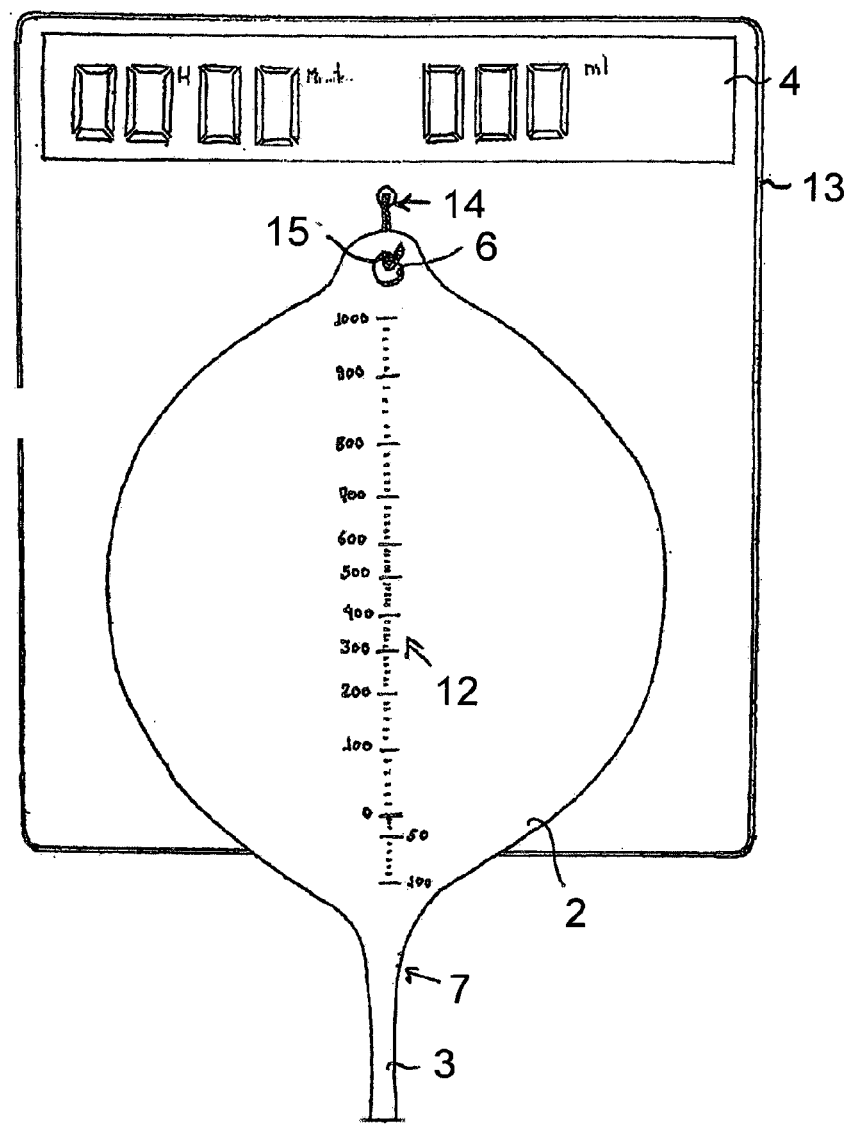
FIG. 3 is an enlarged view of an infusion bag according to the invention.

In FIG. 3 an enlarged view of an infusion bag 2 according to the invention is shown. Presently the infusion bag is located on a holder 15, so that the infusion bag 2 is for example mounted on an IV-stand. The infusion bag 2 has a filling level indicator, from which the filling capacity of the fluid bag 2 can be identified.

Above the infusion bag 2 a dosage instruction 4 is displayed. From this the remaining time period can be identified, in which the infusion fluid inside the fluid bag 2 is dispensed over a patient access 5 to a patient 11.

The infusion bag 2 is mounted using the holder 15 to a scale 13, which comprises the dosage instruction 4 as well as a height adjustment 14. The scale 13 is designed to determine the weight of the infusion bag 2, presently consisting of the weight of the infusion bag 2 and the infusion fluid inside the infusion bag 2. The height adjustment 14 can depending on the determined weight of the infusion bag 2 including the infusion fluid inside the infusion bag 2 adjust the height X, which is present between the infusion bag 2 and the patient access 5 and partly determining the dispensed amount of infusion fluid over the predetermined time period. Therefore for example the holder 15 can be rotatable or pivotable or the holder 15 can be for example adjustable in its height X using an elongated hole and a mechanism connected to the holder 15. Further is could be possible to adjust the height X of a stand, so that the height X of the fluid vessel 2 is adjusted, like shown in FIG. 4*a*.

The measuring of the weight of the infusion bag 2 together with the infusion fluid inside the infusion bag 2 can take place in regular intervals, like e.g. every two minutes. If it is for example provided that 1000 ml infusion fluid is dispensed in 8 hours over a patient access 5 to a patient, every two minutes presently about 1 ml must be dispensed.

To control the dispensed amount of infusion fluid, thus every two minutes a weight measuring of the infusion bag 2 together with the infusion fluid inside the infusion bag 2 can take place and in this way if de facto about 1 ml infusion fluid has been dispensed over the time period of two minutes.

The scale 13 can further comprise a stopwatch, which can for example measure the complete time period until the complete emptying of the infusion bag 2. The scale 13 can also comprise a control lamp, for example a coloured control lamp or control lamps in form of a traffic light, so that using the colours red, yellow and green it can be indicated whether the planned dispensing over the time period is met. Furthermore, a start-button or an on-/off-switch can be provided, which can switch on or off the scale 13 and particularly the measuring of the weight of an infusion bag 2 located at the holder 15. Further, an optical and/or acoustic alarm can be provided, which can alert for example responsible nursing staff in case of an improper dispensing of infusion fluid.

The measuring of the weight can take place using a control unit, which is for example programmed according to specifications, particularly with respect to the parameter that have an influence on the dispensing of the infusion fluid of the infusion bag 2.

In FIG. 4*a* an infusion device 1 according to the invention is shown during the usage with a patient 11. The patient 11 is in a patient bed. The infusion line 3 is connected over a patient access 5 (not shown) connected with the patient 11. FIG. 4*a* shows a height H, in which the fluid vessel 2 of the infusion device 1 is located above the floor. Correspondingly the height X is located between outlet opening 7 of the infusion vessel 2 and the patient access 5 of the patient 11. The difference between height H and height X is identified with height Y.

In FIG. 4*b* a device 1 according to the invention is shown in a top view during the use at a patient 11. As in FIG. 4*a* the patient 11 is in a patient bed. Between the fluid vessel 2 of the infusion device 1 and the patient access 5 in addition to height H a distance D is present, which is presently indicated by the circle drawn in FIG. 4*b*. The total length L of the infusion line consists thus of the height H and the distance D.

FIG. 5 shows a use of an embodiment of a device according to the invention at a patient 11. The patient 11 is in horizontal position, like often present in hospitals.

Using a peripheral venous catheter 5 the device according to the invention is used at a patient 11.

The infusion bag 2 of the device according to the invention is located below the head of the patient 11 and connected to the peripheral venous catheter 5 via infusion line 3.

Between the infusion bag 2 and the peripheral venous catheter 5 located at the hand of the patient 11 presently only a small height difference is present. The patient 11 exercises with his head a pressure onto the infusion bag 2, so that the flow velocity of the infusion fluid inside the infusion bag 2 defined by the height is achieved correspondingly. The dispensing of the fluid in the infusion bag 2 to the patient is achieved in a defined time period.

The solution according to the invention has the advantages over the devices known from the prior art, that a particular easy to use device for the dosed dispensing of an infusion fluid is provided, which is particular easy to use and user friendly due to the predetermined parameters with respect to the dispensing of the infusion fluid contained in the infusion bag 2 over a predetermined time period. Particularly errors, which could occur during adjustment of the complex devices known from the prior art to set the dosing, can be avoided because the dosing of the infusion fluid is predetermined. In addition the device 1 according to the invention is cheap and easy to manufacture, which is particularly advantageous during clinical practise, where a high price pressure exists. The regulation of the flow of the infusion fluid from the fluid vessel 2 for dispensing to a patient access 11 at a patient 11 occurs according to the invention in that at least a sub-section of the infusion line has a predefined inner diameter 8 and a predefined length L, such that the amount of infusion fluid accommodated in the fluid vessel 2 is dispensed to the patient access 5 over a predetermined time period in a manner dependent on a predefined height X at which the fluid vessel 2 is arranged above the patient access 5. From the following table exemplary guidelines can be extracted, which represent the parameter inner diameter 8, length L and height X. Correspondingly an average time period is indicated, which is reproducibly subject to only small deviations in a single-digit percentage range. Reproducible results have been achieved during experiments for water, NaCl 0.9, normal Ringer's solution, glucosamine and glucose as infusion fluid.

The device according to the invention allows regulating the fluid flow without the need of additional devices, which regulate or influence the infusion flow after connecting to a patient. This is achieved by the invention that a regulator device or flow regulator I used. The regulation is influenced by the following parameters:

inner diameter 8 of infusion line 3
length of infusion line 3
height X between fluid vessel 2 and patient access 5
composition of infusion fluid (particularly the viscosity of the infusion fluid) and
ambient temperature.

The following table shows a summary of the predetermined time periods, in which the infusion fluid accommodated in the infusion vessel 2 is dispensed over the patient access 5 to a patient 11. Furthermore, the corresponding data of the used infusion line or the used flow regulator and the corresponding configuration of the infusion device 1 according to the invention are indicated.

The shown and described embodiments of the figures are only exemplary for the invention and not limiting the invention.

| Infusion line data* | Hight difference (X) [m] | Average time [hours] |
|---|---|---|
| 0.9 × 2200 | 0.64 | 8 |
| 0.6 × 370 | 0.76 | 8 |
| 0.6 × 560 | 0.76 | 12 |
| 0.33 × 300 | 0.68 | 12 |
| 0.33 × 600 | 0.68 | 24 |

| Infusion fluid | Flow regulator [mm] | Hight difference (X) [m] | Average time [hours] |
|---|---|---|---|
| Water | 0.9 × 2200 | 0.64 | 08:13:06 |
| NaCl 0.9 | 0.9 × 2200 | 0.64 | 08:09:29 |
| Ringer's solution | 0.9 × 2200 | 0.64 | 08:05:02 |
| Glucosamine | 0.9 × 2200 | 0.64 | 07:57:00 |
| Glucose 5 | 0.9 × 1900 | 0.64 | 08:03:12 |

*= inner diameter [mm] × length (L) [mm]

LIST OF NUMERALS

1 Infusion device
2 Infusion bag/fluid vessel
3 Infusion line
4 Dosage instruction
5 Patient access
6 Holder
7 Discharge opening
8 Inner diameter of infusion line
9 Diameter infusion line
10 Detailed view of infusion line
11 Patient
12 fill level indicator
13 Scale
14 Height control/height adjustment
15 Holder
H Height
X Height between fluid vessel and patient access
L Length of infusion line
Y Difference between H and X
D Distance between infusion device and patient

What is claimed is:

1. A patient infusion device for dosed dispensing of an infusion fluid to a patient, comprising:
a fluid vessel to accommodate the infusion fluid;
a patient access;
an infusion line having an overall length, defined by a first end and a second end, arranged between the fluid vessel and the patient access during use of the device, at least a section of the overall length of the infusion line having a predefined inner diameter and a predefined length;
wherein the fluid vessel, the infusion line and the patient access are in fluid communication with one another and the infusion line is directly connected to the fluid vessel;
wherein the device is a single-use device configured for a one-time use and configured to dispense an amount of infusion fluid from the fluid vessel through the infusion line to the patient access over a predetermined time period in a manner dependent on a predefined height at which the fluid vessel is arranged above the patient access; and
wherein a flow of the infusion fluid through the overall infusion line length is regulated only by the section of the overall infusion line length having the predefined inner diameter and the predefined length itself without an additional regulation device positioned along the overall infusion line length to regulate the flow of the infusion fluid through the infusion line, whereby volumetric flow rate of the infusion fluid from the fluid vessel to the patient is limited by the infusion line;
wherein the fluid vessel includes a predetermined dosage instruction which identifies a predetermined time period over which the infusion fluid of the fluid vessel is dispensed, whereby the predetermined dosage instruction and time period are predetermined independent of the patient;
wherein the fluid vessel includes a reserve volume of the infusion fluid whereby the predetermined time period over which the infusion fluid of the fluid vessel is dispensed is extendable beyond the predetermined time period;
wherein the fluid vessel includes a fill level indicator;
wherein the fill level indicator includes a zero-volume fill level marking;
wherein the fill level indicator comprises a reserve volume fill level indicator;
wherein the reserve volume fill level indicator identifies the reserve volume; and wherein the reserve volume fill level indicator includes at least one reserve volume marking which is below the zero-volume fill level marking and corresponds to a volume of the reserve volume.

2. The device according to claim 1, wherein the infusion vessel and the infusion line are inextricably linked to each other.

3. The device according to claim 1, further comprising a filter arranged between the fluid vessel and the infusion line to filter infusion fluid accommodated in the fluid vessel.

4. The device according to claim 1, wherein the time period, in which the infusion fluid is dispensed to the patient access, is in a range of about 1 litre dispensed in 24 hours to about 1 litre dispensed in 3 hours.

5. The device according to claim 1, wherein the height is in a range of about 60 cm to about 80 cm.

6. The device according to claim 1, wherein the fluid vessel is an infusion bag.

7. The device according to claim 1, wherein the fluid vessel and the infusion line are free of air.

8. The device according to claim 1, wherein the device comprises a vent.

9. The device according to claim 8, wherein the vent is provided by a venting valve.

10. The device according to claim 1, wherein the patient access is a peripheral venous catheter or a central venous catheter or an enteral access.

11. The device according to claim 1, wherein the patient access is inextricably linked with the infusion line.

12. The device according to claim 1, wherein a surface within the infusion line is hydrophilic or hydrophobic.

13. The device according to claim 1, wherein the device comprises a scale which is useable to determine a weight of the fluid vessel.

14. The device according to claim 13, wherein the scale has a display device.

15. The device according to claim 14, wherein the display device is configured to display a weight of the fluid vessel arranged at the scale and/or display a fluid amount of the fluid vessel arranged at the scale.

16. The device according to claim 13, wherein the device comprises an adjustable height stand configured to adjust the height of the fluid vessel above the patient access.

17. The device according to claim 16, wherein the adjustable height stand is configured to adjust the height of the fluid vessel above the patient access as a function of the weight of the fluid vessel, such that the time period in which the infusion fluid is administered to the patient access is adjusted.

18. The device according to claim 13, wherein the weight of the fluid vessel is measurable in predefined intervals, such that the height is adjustable according to a weight change.

19. The device according to claim 1, wherein the predefined inner diameter is in a range from 0.33 mm to 0.9 mm.

20. The device according to claim 1, wherein the fill level indicator sets forth markings identifying a range of volumes.

21. The device according to claim 1, wherein the predetermined dosage instruction identifies the predetermined time period over which the infusion fluid of the fluid vessel is dispensed independent of the reserve volume.

22. The device according to claim 1, wherein the at least one reserve volume marking includes a plurality of reserve volume markings with each marking of the plurality of reserve marking volumes being below the zero-volume fill level marking and corresponding to a respective one of a range of volumes of the reserve volume.

23. The device according to claim 22, wherein each of the markings of the plurality of reserve volume markings is a numeric marking.

24. The device according to claim 1, wherein the at least one reserve volume marking is a numeric marking.

25. A patient infusion device for dosed dispensing of an infusion fluid to a patient, comprising:
a fluid vessel to accommodate the infusion fluid;
a patient access;
an infusion line having an overall length, defined by a first end and a second end, arranged between the fluid vessel and the patient access during use of the device;
a section of the infusion line, having a predefined length less than the overall length of the infusion line, wherein the predefined length has a predefined inner diameter, wherein the predetermined inner diameter is less than a diameter of a further section of the infusion line;
wherein the fluid vessel, the infusion line and the patient access are in fluid communication with one another and the infusion line is directly connected to the fluid vessel;
wherein the device is a single-use device configured for a one-time use and configured to dispense an amount of infusion fluid from the fluid vessel through the infusion line to the patient access over a predetermined time period in a manner dependent on a predefined height at which the fluid vessel is arranged above the patient access; and
wherein a flow of the infusion fluid through the overall infusion line length is regulated only by the section of the overall infusion line length having the predefined inner diameter and the predefined length itself without an additional regulation device positioned along the overall infusion line length to regulate the flow of the infusion fluid through the infusion line, whereby volumetric flow rate of the infusion fluid from the fluid vessel to the patient is limited by the infusion line;
wherein the fluid vessel includes a predetermined dosage instruction which identifies a predetermined time period over which the infusion fluid of the fluid vessel is dispensed, whereby the predetermined dosage instruction and time period are predetermined independent of the patient;
wherein the fluid vessel includes a reserve volume of the infusion fluid whereby the predetermined time period over which the infusion fluid of the fluid vessel is dispensed is extendable beyond the predetermined time period;
wherein the fluid vessel includes a fill level indicator;
wherein the fill level indicator includes a zero-volume fill level marking;
wherein the fill level indicator includes a reserve volume fill level indicator;
wherein the reserve volume fill level indicator identifies the reserve volume; and
wherein the reserve volume fill level indicator includes at least one reserve volume marking which is below the zero-volume fill level marking and corresponds to a volume of the reserve volume.

26. The device according to claim 25, wherein the predefined inner diameter is in a range from 0.33 mm to 0.9 mm.

* * * * *